United States Patent [19]

Dulout et al.

[11] 4,199,450
[45] Apr. 22, 1980

[54] PROCESS OF SEPARATING FROM AN AQUEOUS MEDIUM A PROTEIN OR A MORPHOLOGICALLY ORGANIZED UNIT BY LIQUID EXCLUSION CHROMATOGRAPHY

[75] Inventors: Charles Dulout, Carrieres; André Peyrouset, Ger; René Panaris, Pau; Claude Hannoun, Meudon; Jean Vincent, Pau, all of France

[73] Assignees: Societe Nationale Elf Aquitaine (Production); Institut Pasteur, both of Paris, France

[21] Appl. No.: 900,081

[22] Filed: Apr. 26, 1978

[30] Foreign Application Priority Data

Apr. 26, 1977 [FR] France .............................. 77 12518
Apr. 12, 1978 [FR] France .............................. 78 10769

[51] Int. Cl.$^2$ .............................................. B01D 15/08
[52] U.S. Cl. ................................... 210/31 C; 195/1.5; 260/112 R; 435/239
[58] Field of Search ........................ 210/31 C, 198 C; 23/230 B; 195/1, 1.5; 260/112 A

[56] References Cited

U.S. PATENT DOCUMENTS

| | | | |
|---|---|---|---|
| 3,467,595 | 9/1969 | Sten | 210/31 C |
| 3,476,737 | 11/1969 | Emneus et al. | 210/31 C |
| 3,549,524 | 12/1970 | Haller | 210/31 C |
| 3,701,609 | 10/1972 | Bailey | 210/198 C |
| 3,926,800 | 12/1975 | Stephens | 210/198 C |
| 4,123,931 | 11/1978 | Blaser | 210/31 C |

*Primary Examiner*—John Adee
*Attorney, Agent, or Firm*—Ostrolenk, Faber, Gerb & Soffen

[57] ABSTRACT

A novel process of separating from an aqueous medium at least one protein or at least one morphologically organized unit by liquid exclusion chromatography on a solid support previously passivated by treatment with an aqueous solution of a non-proteinic polymer. In this process, the chromatographic support is submitted, prior to the chromatographic operation, to a second passivation consisting in contacting the support with an aqueous solution of a protein which has a molecular weight lower than that of the protein to be separated, and which is adapted to be adsorbed by said support. The support and/or the liquid to be treated are sterilized with antiseptic agent selected from the group constituted by the lower aliphatic halogenated hydrocarbons.

18 Claims, 4 Drawing Figures

PROCESS OF SEPARATING FROM AN AQUEOUS MEDIUM A PROTEIN OR A MORPHOLOGICALLY ORGANIZED UNIT BY LIQUID EXCLUSION CHROMATOGRAPHY

The present invention relates to an improved process of separating and purifying proteins having very different molecular weights and being possibly present in the form of morphologically organized units; according to this invention, the liquid chromatographic exclusion method is used. The invention applies particularly to the separation and/or purification of viruses, starting from a virus culture medium or from a medium which has previously been concentrated and partially purified; thus the invention may advantageously be applied to the separation and the purification of the infuenza viruses. The invention also relates to a device for carrying out the above mentioned process on an industrial scale.

In spite of the successful application of the chromatographic methods in the fields of analyzing and extracting various substances, these methods could not up to now be applied with advantage to the industrial treatment of proteins having a low and a very high molecular weight; this applies, more particularly, to the viruses. The application of exclusion chromatography to the purification and the separation of soluble macromolecules or of macromolecules organized in the form of more or less complex morphologic units, such as lipidic micelles, organized fractions of bacterial bodies or viruses has been described in various publications. Thus, an improved purity of proteins, particularly of viruses, has been obtained due to the application of supple gel exclusion chromatography, especially using agar spheres (cf. Bentsson and Philipson Biochim. Biophys. Acta 79 (399) 1964); however, since these supports present comparatively poor mechanical resistance properties, or mechanical strength, they do not allow very satisfactory results to be obtained from an economical viewpoint when it is attempted to use such supports on an industrial scale where high flow rates corresponding to comparatively high pressures have to be applied to the chromatographic column. Furthermore, these gels do not support sterilization by heat, which brings about a limitation of their use for separating products that must be preserved in a sterilized state. It is also known to use in exclusion or affinity chromatography, rigid supports siuch as glass spheres; such supports have the advantage of presenting satisfactory mechanical strength properties and of being able to support high pressures; they are also advantageous in that they can be sterilized prior to utilisation. These supports have, however, one drawback which resides in the fact that they adsorb considerable amounts of proteins; this drawback has been minimized by pre-treating the support with reagents which block the active adsorbent sites of the support; thus it is known to treat such supports with polyethylene glycol; however, this known treatment does not allow stable results to be obtained, and the active sites reappear progressively during the treatment.

It should also be noted that according to the prior art (Analytical Biochemistry 58, 30–38, 1974) proteins could not be separated by the liquid exclusion chromatography method using porous silica gel unless high pressures on the order of several tens of bars were applied. Furthermore, this method only applied to proteins having a molecular weight of 250,000 to 800,000, and only in the field of analysis. The problem was not solved when it was decided to separate on an industrial scale under pressures close to atmospheric pressure proteins having a very high molecular weight, especially a molecular weight of more than one million, which is the case, in particular, of the influenza virus, the average molecular weights are higher than several millions.

This problem is solved by the present invention which allows proteins having a very high molecular weight, on the order of several millions, as well as proteins having a molecular weight comprised between about 10,000 and one million, to be efficiently separated.

Various processes of separating and purifying viruses are also known. Some of these processes comprise separating the viruses by density in a continuous manner by means of an ultra-centrifuging device, the viruses being capted in a continuous saccharose gradient. Other known processes comprise a step of specific adsorption, especially on erythrocytes or on a non-soluble complex of polymer and bi-valent salts, followed by a desorption step, or such known processes comprise a step of adsorption on insoluble salts, such as calcium phosphate or baryum sulphate, or a simple precipitation step, e.g. by means of ammonium sulphate, polyethylene glycol and organic solvents. These processes in combination, which are at present industrial processes, still do not allow satisfactorily purified products to be obtained. It may thus be necessary to perform consecutive treatments using solvents which denature the proteins and dissolve the lipids. Furthermore, these known processes do not allow an optimum yield to be achieved.

Due to the present invention, it is possible to improve the separation and the purification of proteins by using the exclusion chromatography method which is performed in a novel manner. The invention allows the drawbacks of the known processes to be overcome, and the process according to the invention may advantageously be combined with known industrial means. The process according to the invention can be carried out on an industrial scale and allows a yield of approximately 100% to be achieved.

The expression of "protein", as used in the present description, also includes morphologically organized units, especially viruses, which can be extracted from the medium in which they are contained, with a very high purity. The novel process and its variants allow, in particular, excellent results to be obtained in the field of separating and purifying influenza viruses specially multiplied on embryonized eggs or on cellular substrates cultivated in vitro.

In the process according to the invention, the charge or support of an exclusion chromatography column is submitted, prior to its use, to two passivation steps, the first passivation step being carried out by means of an aqueous solution of a non-proteinic polymer, in a manner known per se, and the second passivation step being carried out by means of an aqueous solution of a protein having a molecular weight lower than that of the protein to be separated, said protein of low molecular weight being adapted to be adsorbed by the charge. The expression of "passivation" means that the particles of the charge are contacted with a reagent adapted to block the adsorbent sites of said charge.

As already set forth herein-above, the known methods of passivation, especially the methods using polyethylene glycol, allow no stable results to be obtained; in contradistinction thereto, the active sites of the charge do not reappear during operation when a supplementary passivation by means of a protein has been effected.

In the process according to the invention, the chromatographic charge may be constituted by silica or by a silicate, especially by silica gel or glass spheres, i.e. a silicate of an alkali metal. The porous diameter is preferably comprised between 5 and 200 nm, and the specific surface for particles of 40 to 200 microns is 500 to 20 $m^2/g$, respectively.

When the medium containing the protein to be separated has passed through this support, the product is eluted with water at a buffered pH of 5.5 to 7.5, at a temperature of 0°–30° C., preferably 4° to 20° C., and under a pressure corresponding to the pressure drop in the column. The eluent preferably has a pH close to 7, this pH value being comprised in practice between 6.5 and 7.5. The pressure generally is comprised between 1 and 2 bars.

The nature of the buffer must, of course, be compatible with that of the proteins to be treated, with a view to preventing the latter from precipitating or from being altered. Buffers known per se such as buffers on the basis of alkaline phosphates may advantageously be used to this end. Furthermore, the elution water advantageously contains also a strong electrolyte, for example sodium chloride, in a concentration of 0.1 to 0.2 M.

Silica gels which may be used when carrying out the process according to the invention are commercially available under the designation of "Sphérosil". Any other gel of similar quality or glass spheres may also be used.

When the above-described operating conditions are complied with, it is possible to use columns the inner diameter of which is comprised between 8 and 200 mm, such columns being able to work with flow rates of 3 to 30 l/h, which values correspond to biological production on an industrial scale. The height of the column depends on the nature of the product to be separated and purified, on the properties of the support and on the chromatographic curve of the system considered; the height may, for example, be comprised between 0.5 and 2 m.

The process according to the invention may advantageously be carried out by means of a plurality of columns mounted in series and possibly loaded with different supports of the kind indicated herein-above, which have different characteristics. It is thus possible to separate different proteins from each other and to complete the purification of a given product.

As in the known processes, the polymer used in the first step of passivation of the chromatographic support may be a water-soluble aliphatic compound, especially a compound containing hydroxyl groups, such as polyethylene-glycol, polypropylene-glycol, polybutylene-glycol, polyvinyl alcohol, polyvinylpyrrolidone, (polyethylenepolypropylene)-glycol copolymer, etc. Preferably, the molecular weight of such blocking agent is comprised between about 5,000 and about 30,000.

The blocking of the adsorbent sites of the support is effected by passing an aqueous solution of the selected reagent, for example, polyethylene glycol having a molecular weight of 20,000, rather highly diluted (e.g. 0.5 to 5 g/l), through the charge of the column. The volume of this solution must be equal to several times the volume of the charge. Conveniently, the volume of said solution may be equal to about 10 times the volume of the charge. However, this passivation is not sufficient, and part of the proteins or products to be separated remain fixed on the support if the second passivation in accordance with the invention is not effected. This second passivation is carried out by treating the chromatographic support with an aqueous solution of one or more proteins having a molecular weight lower than that of the protein to be separated. Depending on the nature of the proteins to be separated, various industrially available proteins may be used, for example, albumin serum, ovalbumin or lactalbumin, gelatin, peptones, etc. It is advantageous to use the lighter protein which accompanies the heavier protein to be separated. Products of degradation of various polypeptides may be used. Generally, the molecular weight of the passivating protein, or proteins, is preferably lower than 100,000 and, still more advantageously, is not higher than 50,000. The solution may contain 0.2 to 20% by weight of passivating protein; preferably the passivating protein content is comprised between 1 and 15%. In the case of the separation and purification of influenza viruses, excellent results are obtained by applying one or more times allantoic liquid from embryonized eggs which had not been infected with the influenza virus. Under these conditions, the silica gel column has lost entirely its virus fixation capacity; it is stable and can operate for months using the buffered eluant for extracting the desired morphologically organised units without any adsorption of the latter by the silica or the silicate.

The process and the device according to the invention allow highly pure proteinic products to be obtained, starting from aqueous media, and, more particularly, viruses to be obtained from the culture medium of these micro-organisms. However, on account of the mechanism of the exclusion chromatographic method which comprises eluting with more or less large volumes of liquid, the concentration of the desired protein in the purified solution obtained is generally not very high. when the envisaged use does not require a very highly concentrated solution, the product obtained as described herein-above is entirely satisfactory; on the contrary, when higher concentrations are required, these can be achieved in accordance with a variant of the instant process.

Variants of the process according to the invention consist in combinations of the liquid exclusion chromatography method with various purification methods, such as precipitation, adsorption and/or ultra-centrifugation. These variants of the instant process may be carried out in two ways; The desired protein is first concentrated and/or purified by one of the known methods indicated hereinabove, so as to produce a concentrated and/or semi-purified solution of the desired product; this product is then extracted in the purified state by chromatography; or else the starting medium is submitted to exclusion chromatography for separating the desired products in a state of satisfactory purity; the thus obtained solution is then concentrated, the desired product is extracted and then purified by one of the above-mentioned methods.

Thus, in the case of the separation of the influenza virus from allantoic solutions, the first step may be the concentration of the virus by adsorption-desorption on red blood corpuscles; adsorption on calcium phosphate, then sorting out by complexing the calcium; precipitation by means of salts such as $BaSO_4$ or $(NH_4)_2SO_4$ or by means of polyethylene glycol or another poly-(oxyalkene); zonal density gradient ultra-centrifugation;

adsorption on porous glass or silica gel followed by desorption by raising the pH; ultrafiltration on diaphragms or hollow fibers; alternatively, the separation of the virus is first effected by exclusion chromatography in accordance with the invention, whereafter the solution of this virus is concentrated by one these methods or by lyophilisation.

One advantageous process carried out in combination with chromatography comprises semi-specific adsorption by adding to the liquid containing the purified or non-purified virus polyalkylene-glycol or poly-(oxyalkene), more particularly polyethylene-glycol, and a bivalent salt, especially calcium chloride. The insoluble polymer—$Ca^{++}$ complex which, during its insolubilisation has carried off the viruses, is dissolved again in an aqueous solution of ethylene-diaminotetra-acetic acid or of an alkaline salt of the latter (especially the sodium salt), or in an aqueous solution of any other agent capable of decomplexing the calcium.

The thus obtained concentrated solution is then submitted to the above-described exclusion chromatography treatment. The result is a solution which is concentrated as well as extremely pure.

Although the principle of this method is known per se (cf. Ph. Adamowicz, B. Legrand, J. Guerche and P. Prunet; Bull. off. int. Epiz 1974, 8&, (11-12), 1125, 1150), its combination with the chromatographic purification according to the invention involves an adaptation without which the results obtained would not be satisfactory. Indeed, according to the known method, the polyethylene-glycol used together with the bivalent metal salt for forming the complex must have a molecular weight of at least 100,000, up to 300,000. In contradistinction thereto, in accordance with the present invention, polymers having considerably lower molecular weights must be used since when polymers of a molecular weight of 100,000 or more are used, the chromatographic operation may be impeded by the high viscosity and lead to obtaining less pure preparations, since the polymer is less efficiently separated from the viruses. In accordance with the invention, the alkaline oxide polymer used must have a polymerization degree limited to about 80–1,400, which in the case of polyethyleneglycol corresponds to molecular weights of about 5,000 to 85,000; preferred molecular weights are comprised between 6,000 and 30,000 and, more particularly, between 10,000 and 25,000. Equivalent results have also been obtained when using the previously indicated polymers.

The novel process and its variants allow excellent results to be obtained when preparing concentrated solutions of pure influenza viruses. Generally, the influenza viruses which are to be used for preparing vaccines are multiplied in the allentoic cavity of embryonized chicken eggs. During the collecting operation, the allentoic liquids which are already loaded with various proteins and salts may be contaminated with the phospholipids collected accidentally by alteration of the vitelline membrane. The pure influenza viruses are extracted from this culture medium. These viruses have the property of agglutinating the red blood corpuscles of chicken, which allows said viruses to be rapidly and quantitatively determined; the result of such determination can be expressed in international hemagglutination units.

Since the proteins are generally quite sensitive to attacks by micro-organisms, especially the proteins of biological media from which enzymes, viruses, etc. are extracted, the treatment of the medium submitted to the separating peration must be carried out under sterile conditions. The conventional sterilization of the apparatus used, especially by heat, involves dismounting the apparatus, when the latter had industrial dimensions and is of industrial construction; furthermore, this operation does not allow contamination during the work to be avoided. According to the conventional method, one or more antiseptic substances, especially formaldehyde or sodium merthiolate (sodium-ethyl-mercuri-thiosalycilate) are added to the liquid to be treated. This allows an acceptable sterilization to be effected, but especially in the case of viruses, the antigen obtained is inactivated. Consequently, the conventional method can not be used in the preparation of a living vaccine under sterile conditions.

These drawbacks of the prior art are overcome by a variant of the process according to the present invention. This variant enables to prevent permanently the proliferation of bacteria during the entire duration of the operations of protein separation without inactivating the virus to be separated. Thus, the process according to the invention may most advantageously be applied to the general case of the non-living proteins as well as to the case of the separation of viruses. This latter case is more important in the field of serology, as is well known. Consequently, the process according to the invention allows living vaccines to be easily prepared.

This variant is characterized by the special selection of an antiseptic agent adapted to act selectively as a bactericidal or at least bacteriostatic agent, while being inoffensive with respect to morphologically organised proteinic units which are to be separated. According to the invention, such agents are selected from the group constituted by the lower aliphatic halogenated hydrocarbons. It is particularly advantageous to use di- and tri-halogenated hydrocarbons, especially the latter. Depending on the nature of the units, especially the viruses which must not be attacked, and depending on the sensitivity of the same with respect to the halogenated hydrocarbons, it is possible to use as antiseptic substances one or more compounds such as mono-, di-, tri- and tetrachloromethane, mono-, di-, tri- and tetrachloroethane, mono-, di-, tri- and tetrachloropropane, or the corresponding brominated or iodinated derivatives, provided that their solubility in water is at least equal to 0.1 g/l and preferably equal to or higher than 1 g/l. The proportion of antiseptic agent used is comprised in the limits of the solubility of the agent in water. Furthermore, the agent used must have a high vapour pressure so that it can easily be eliminated from the finished product.

Although compounds such as methylchloride, bromide or iodide, having a comparatively low solubility in water may be used, it is recommended to use halogenated hydrocarbons with a solubility in water of about 1 to 10 g/l. The following compounds which are part of this category are indicated by way of example: dichloromethane, dibromomethane, di-iodomethane, dichloroethanes-1,2 (cis and trans), dibromoethane-1,2, trichloromethane (chloroform), tribromomethane (bromoform), trichloroethane-1,1,2, trichloroethylene, etc.

In certain cases, iodoform ($CHI_3$), which has been widely used in the past in surgery, may also be used, but on account of its low solubility (about 0.1 g/l) and of its comparatively high toxicity ($LD_{50}$ 630 mg/kg, mouse), it is preferable to use chloroform ($CHCl_3$) which allows remarkable results to be obtained, its solubility in water being equal to about 5-7 g/l at moderate temperatures.

Since the halogenated hydrocarbons are excellent solvents for the lipids, one was entitled to expect that they affected the micro-organisms the envelope of which is of a lipidic nature. Now, most surprisingly, it has been observed that such action takes not place when the antiseptic agents according to the invention are used provided that the amounts remain within the limits of the solubility of these agents. Thus, for example, chloroform in a concentration of about 5 g/l of medium containing an influenza virus does not affect at all said virus, while efficiently sterilizing the solution with regards to the bacteria. When such concentration is used neither the infection ratio nor the hemoagglutinant power of the virus are modified, even after five days of incubation. Consequently, it becomes apparent that in spite of the old knowledge regarding the antiseptic effect of certain above-mentioned halogenated hydrocarbons, the application according to the invention is entirely novel and could not have been foreseen.

The antiseptic agents according to the invention can be added to the liquid to be treated, to the buffer solution used for elution or to both these media. When the solution of the separated protein is lyophilized, this operation eliminates the very small amount of halogenated hydrocarbon which might have been retained in the protein.

The present invention will be described hereinbelow, by way of example but not of limitation, with reference to the appended drawings.

Exclusion chromatography devices for preparing various substances are known, however, the known devices could be used only for analysis, the columns of these devices having an inner diameter of about 8 mm. Up to now, no high-capacity automatic chromatographic material has been known.

Figure 4:
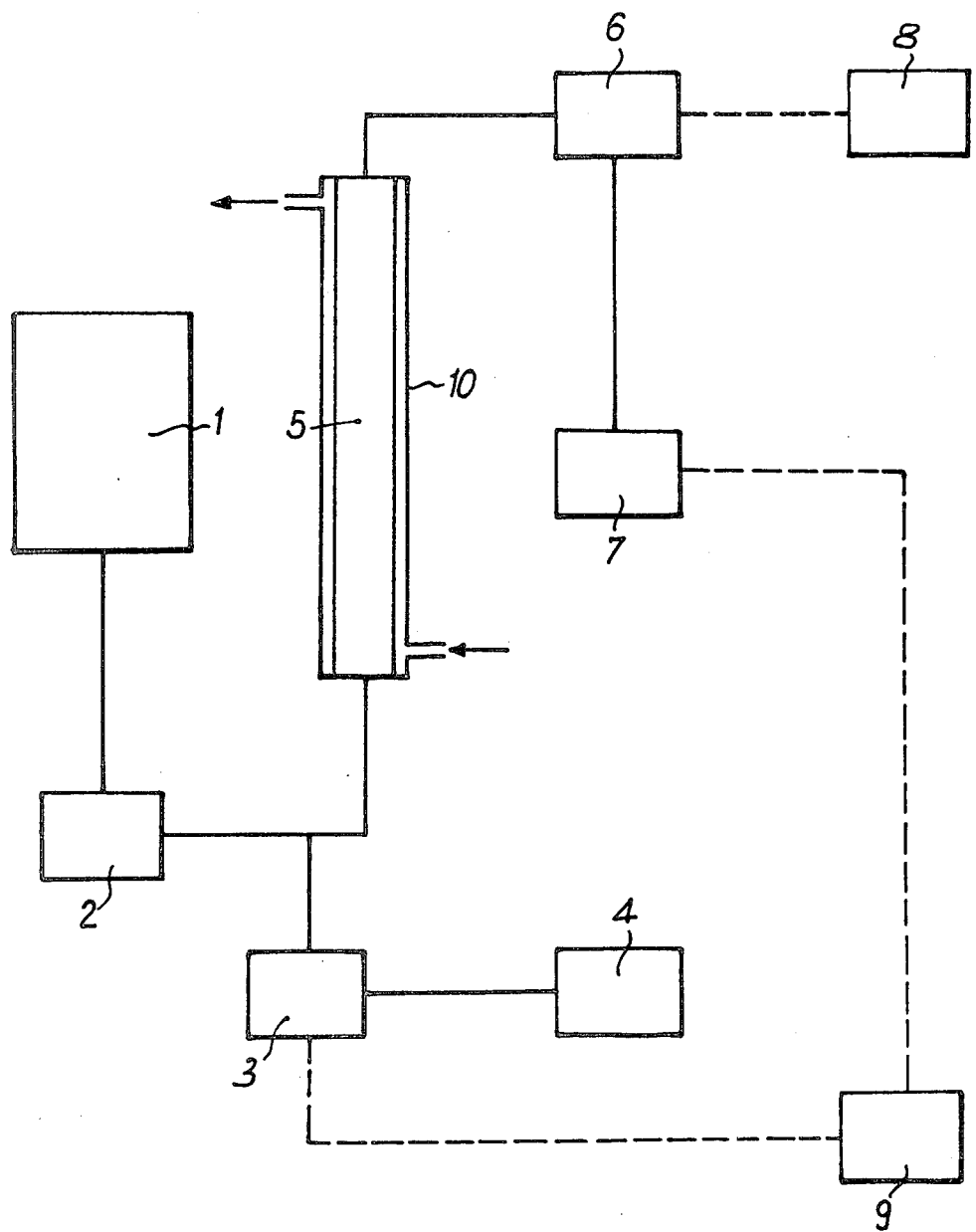
FIG. 4 shows schematically the chromatographic device used in the operations described in the examples.

The device for industrial production in accordance with the invention is shown in FIG. 4. A pump 2 permanently pumps the eluting solvent contained in reservoir 1 into column 5. The solution to be fractionated, which is contained in reservoir 4, is injected into column 5 at regular time intervals by an automatic system 3 constituted by electro-valves and a sampling loop of 500 ml for example. Column 5 which has a high capacity—its diameter being, for example, equal to 10 cm and its height equal to 120 cm—is made of stainless steel. Said column is surrounded by a double envelope 10 also made of stainless steel and capable of withstanding sterilization pressures when sterilized by means of vapour, said envelope further being connected to a coolant circuit (e.g. plus 4° C.). Silica gel is placed within column 5. Products issuing from chromatography can be collected in selected fractions, and the control of the effluent of the column is effected by means of an ultra-violet detector 6 the response signal of which is transmitted to a recorder 8. The various eluted products are collected in a fraction collector 7 constituted by an automatic valve having n ways (e.g. 20 ways), said collector being constituted, more particularly, by an assembly of electrovalves. The various operations, such as injections, and collecting operations are carried out automatically by means of a conventional programming device 9. This apparatus is able to operate continuously during 24 hours per day.

It is possible to treat with the device described hereinabove 450 up to 500 mm of liquid per hour, which corresponds to an amount of 10.8 to 12 liters per day, for obtaining a perfectly purified product. In the case of the purification of influenza virus, 12 liters of allentoic liquid can be treated per day. This shows the advantage of the described variant according to which a previously concentrated and partially purified liquid is treated in the column. Since it is possible to concentrate the allentoic liquid 40 times, the quantity of allentoic liquid stemming from eggs, which can be treated, amounts to 400-480 liters, which corresponds to the production on the basis of about 60,000 eggs.

The invention will now be described, by way of illustration but not of limitation, by the following examples.

EXAMPLE 1

Preparation of the column

The above described column has an inner diameter of 10 cm and a height of 120 cm. It is loaded with silica gel powder having particles of 100-200 microns, with an average core diameter of 60 nm and a specific surface of 50 $m^2/g$, the apparent volume of the charge being 1 ml/g. The silica gel used is the one sold by the firm RHONE-POULENC under the commercial designation of "SPEROSIL XOB 030". After sterilization by vapour, the gel placed into the column is submitted to a first passivation, i.e. said gel is treated with a 1% aqueous solution of polyethylene glycol having a molecular weight of 20,000, for blocking the adsorbent sites, said treatment being carried out during 24 hours. The column then receives a charge of 500 ml of allentoic liquid which is not loaded with influenza viruses; this operation constitutes the second passivation. This double passivation is followed by rinsing with an aqueous buffer solution of monobasic potassium phosphate and dibasic sodium phosphate, said solution being sterilized, having a pH of 7.5 and containing NaCl in a concentration of 0.15 M. The column is now ready to be used for the treatment of solutions of products to be purified.

EXAMPLE 2

Separation of the influenza virus, strain A/X-53, from its allentoic culture medium The treated virus solution stems from the conventional culture in the allentoic cavity of the embryonized chicken egg, after 10 to 12 days of incubation; said solution has a specific content of 1200 HA units (hemato-agglutination method) per 0.25 ml.

450 ml of said solution are injected into the column with a flow rate of 150 ml per minute, i.e. during 3 minutes, which operation is repeated once per hour. During this time, a certain amount of the above-mentioned buffer solution is made to flow continuously through the column. As long as only the virus appears at the outlet of the column, the flow rate of the buffer solution is 9 l/h. With this flow rate, the virus starts to appear after 30 minutes; the flow rate is trebled, i.e. increased to 27 l/h, when the eluate starts to contain the impurities of the virus. This mode of operation allows the operation to be performed in a shorter time, for example, within one hour.

Since the column is provided with automatic devices known per se, it is possible to operate said colum without interruption during any desired period of time.

The detection of the components of the eluate at the outlet of the column is effected by means of a device for determining the optical density in ultra-violet radiation having a wave-length of 252 nm; as such device is well known per se by those skilled in the art, it will not be described herein in more detail.

As the pressure drop through the column is comparatively low, circulating the solution through said column requires only a pressure of about 1 bar above atmospheric pressure at the inlet of the column.

The 450 ml of virus solution treated yield after chromatography 1050 ml of eluate containing highly pure virus, whereas the impurities are contained in the remainder of the buffer solution flowing through the column.

Figure 1:
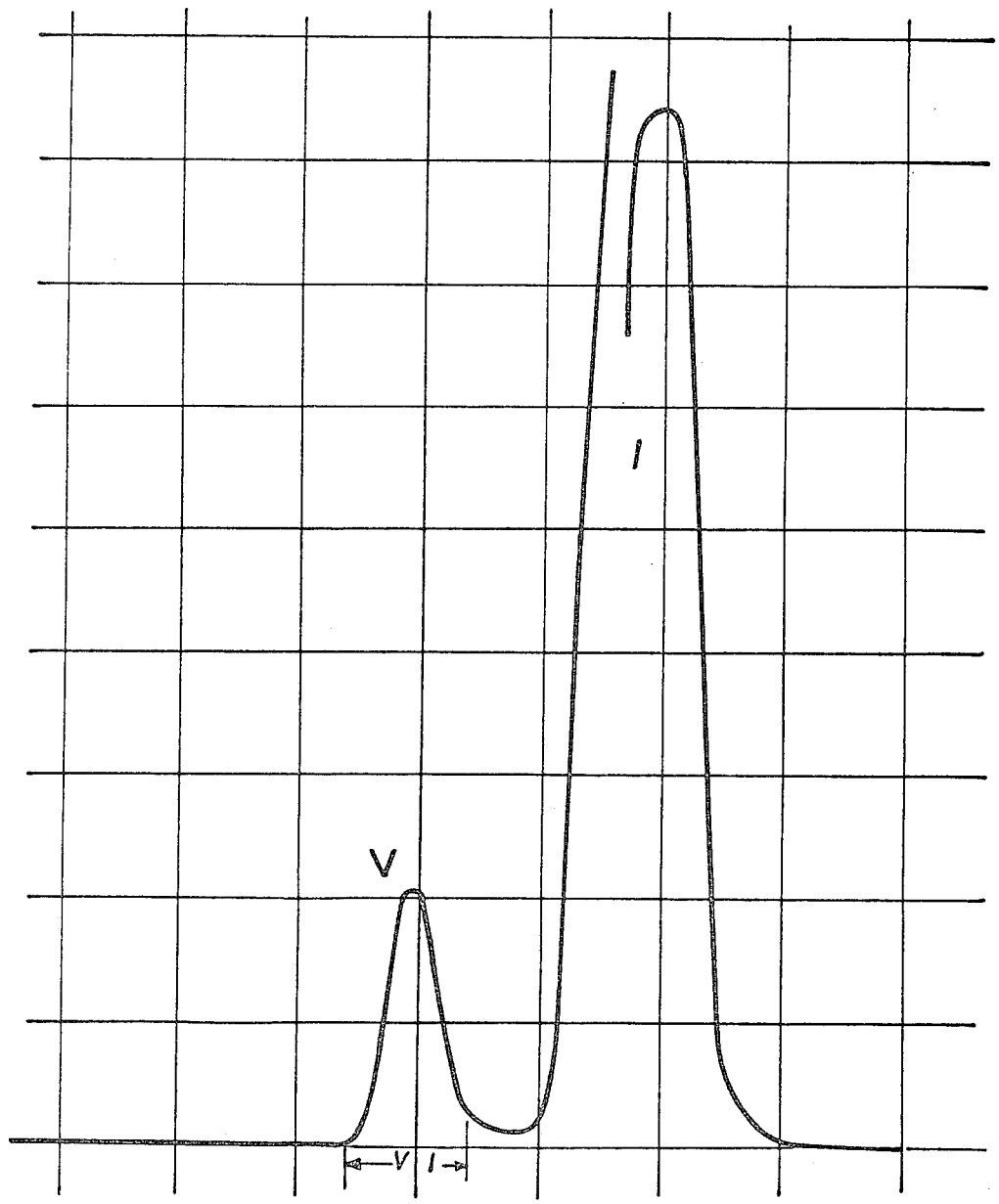
FIG. 1 shows the chromatographic curve corresponding to the separation of influenza viruses.
Figure 2:
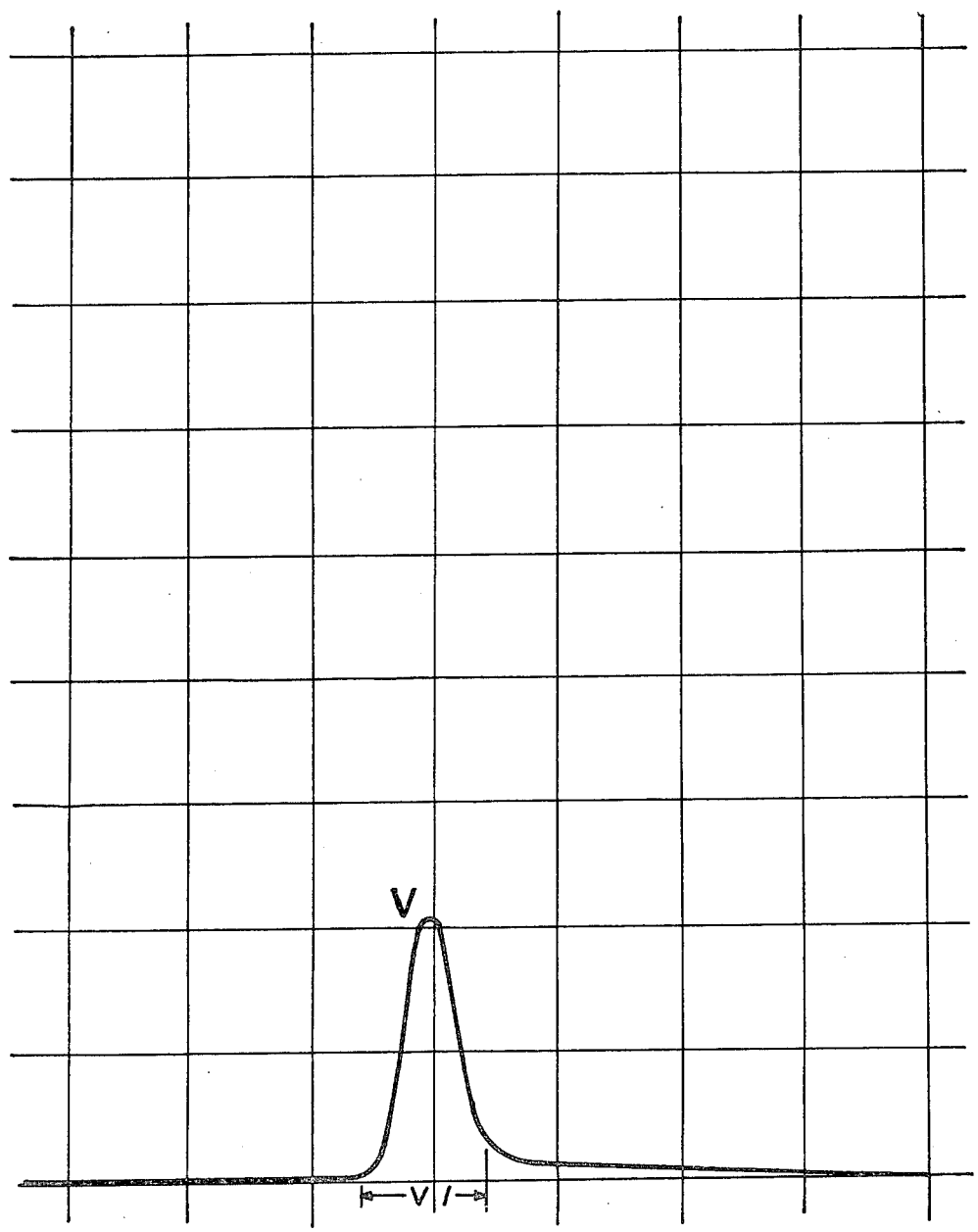
FIG. 2 is the chromatographic curve of the purified virus solution according to FIG. 1.

According to FIG. 1 which shows the chromatographic curve of this operation (the optical density being represented by the ordinates, and the volume of eluate being represented by the abscissae) clearly indicated the V peak corresponding to the virus and the I peak corresponding to the impurities. The discontinuity of the I peak is due to variation of the flow rate from 9 to 27 l/h. When a 3 ml sample taken from the 1050 ml of purified solution is examined in an analytical chromatographic column having a diameter of 0.10 cm and a height of 120 cm, loaded with the abovedescribed silica charge, only a virus peak will appear (cf. FIG. 2), no impurities at all will be present.

This shows that the virus has been perfectly purified.

The final result of the operation, as determined by the measurements of the activity according to the hemoagglutination method (HA) will be given herein-below. The 450 ml of starting allentoic solution had a specific content of 1200 HA units per 0.25 ml, while the activity of the 1050 ml obtained corresponded to 480 HA units per 0.25 ml. Thus, at a start, 2,160,000 HA units were present, and 2,016,000 HA units were found in the purified solution. It can consequently be seen that the yield amounts to:

$$(2,016,000 \div 2,160,000) \times 100 = 93.3\%$$

which value is to be considered as extremely elevated, since the known methods give considerably lesser results.

EXAMPLE 3

Separation of influenza virus by a double adsorption elution on erythrocytes followed by chromatographic purification on silica gel 50 liters of virulent allentoic liquid stemming from chicken eggs embryonized since 10 to 12 days are previously clarified by centrifugation in a manner known per se, for eliminating the insoluble substances. The centrifugated liquid contains 1200 HA units per 0.25 ml.

4% (V/V) of a cake of red blood corpuscles from chicken are added to this suspension. After a contact time of 8 to 16 hours at a temperature of +4° C. or +37° C., the erythrocytes are separated by centrifugation at 3,000 RPM and the virus is eluted with a phosphate buffer the volume of which is 5 liters. The eluate has a specific content of 12,000 HA units per 0.25 ml.

450 ml of this virus suspension are injected automatically into the column within 3 minutes, with a flow rate of 150 mm/min. During this period of time, the buffer solution described in Example 1 is made to flow permanently through the column. The flow rate of this buffer solution is 9 l/h as long as only the virus appears at the outlet of the column. The flow rate is trebled, i.e. increased to 27 l/h, when the eluate does no longer contain viruses, but contains contaminated proteins. Each operation lasts one hour. Due to its automatic equipment, a column operates continuously until the 5 liters of concentrated eluate have been consumed. The peaks corresponding to the purified viruses are collected and result in a volume of 15 liters. Their specific content is 3,200 HA units per 0.25 ml, which corresponds to a yield of about 100%.

EXAMPLE 4

Starting from 10 liters of a solution of allentoic liquid infected with influenza virus, similar to the solution used in Example 2, a first concentration-purification on polymer-calcium complex is carried out. For this purpose, 2% by weight of polyethylene-glycol having a molecular weight of 20,000 and 12 g of powderous $CaCl_2$ are added to this aqueous solution. After mixing during 30 minutes for producing a homogeneous mixture, the precipitate is separated by decantation, whereafter a centrifugation step is performed. The precipitate is then picked up with a view to eluting the virus in about 500 ml of an aqueous solution of 0.2 M of the dibasic sodium salt of ethylene-diamino-tetraacetic acid, adjusted to pH 7.5 by adding 6 N-sodium hydroxide.

The solution thus obtained is centrifugated with a view to elminating the insoluble matter, and the supernatent clear liquid—in an amount of about 500 ml—is kept.

It has been found that the yield of such concentration-purification operation is approximately 65%.

The 500 ml of the above-mentioned concentrated solution are submitted to exclusion chromatography in a column having an inner diameter of 10 cm and a height of 110 cm, said column being loaded with the silica described in Example 1; the same buffer solution as the one described herein-above is used. The 500 ml of solution are injected as described in Example 2. The virus peak is collected by elution in 1,500 ml of a solution having a specific content of 10,800 HA units per 0.25 ml, which corresponds to a purification yield of about 98%. The virus solution thus obtained is highly concentrated as well as extremely pure.

EXAMPLE 5

Infected allantoic liquid such as described herein-above is concentrated by diafiltration on diaphragms or hollow fibers having a rupture point of $1.10^6$.50 liters are thus reduced to a volume of 5 liters or less. After clarification, this concentrate is injected directly in a column corresponding to the model described in the preceding Examples, this injection being carried out in accordance with the method described.

The virus peak contains all of the hemagglutinant units which have been deposited. This solution, which is very pure from a proteinic viewpoint, may still be contaminated by phospholipids of the vitelline bag, organized in the form of micelles. This contaminating substance can be separated by density by means of ultracentrifugation on a saccharose gradient. All of the impurities having been eliminated by exclusion chromatography, the yield of the operation is considerably improved.

EXAMPLE 6

500 liters of infected allantoic liquid such as described hereinabove are purified by a first operation of ultra-centrifugation on a saccharose gradient.

A collected virus peak represents a volume of one liter. The yield of this operation is comprised between 30 and 80%.

The virus peak is introduced automatically in a silica gel column similar to that described in Example 2, and exclusion chromatography is effected by the process described also in Example 2.

The collected volume equals 3 liters.

The yield of the chromatography operation is approximately 100%, as before, whereas the treated liquid contained still a substantial proportion of contaminating proteinic substances.

EXAMPLE 7

The operations carried out in accordance with this Example are similar to those described in Examples 2, 3, 4, 5 and 6. However, the virus suspension submitted to exclusion chromatography is previously inactivated by means of formol, of β-propiolactone or of ultra-violet radiation, and are treated with an organic solvent.

EXAMPLE 8

Figure 3:
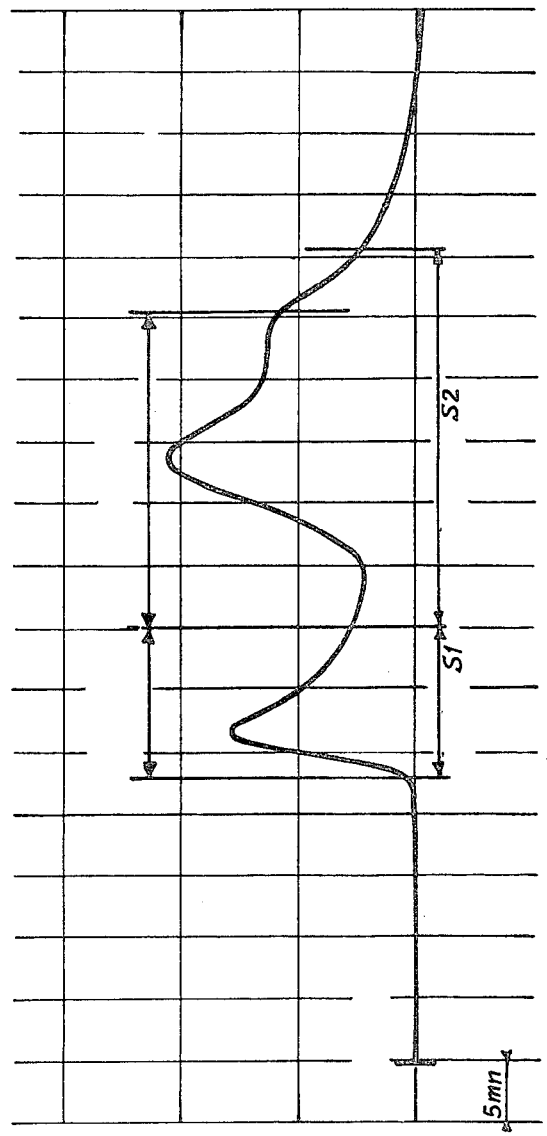
FIG. 3 is the chromatogram of a purified catalase solution prepared by the process according to the invention.

The chromatography column prepared as indicated in Example 1 is used for purifying an aqueous solution of catalase loaded with impurities which has been extracted by preliminary operations from beef liver. This solution has an activity of 220 International Units. The eluant is buffered to pH 7. A solution having an activity of 180 International Units is obtained, which corresponds to a yield of 86% in the $S_1$ of the chromatogram represented in FIG. 3.

EXAMPLE 9

The operations described in Example 2 are repeated, using the column described in Example 1, however, the charge of the column is constituted by glass spheres having dimensions comprised between about 80 and 280 microns, the average porous diameter being 50 mn.

The purified virus yield is 87%.

EXAMPLE 10

The virus of the B/HK strain is purified in accordance with Examples 1 and 2; however, the second passivation of the charge of the column is carried out by means of 500 ml of a 6% aqueous solution of lactalbumine having a molecular weight of about 18,000.

The yield of these operations is 92%.

EXAMPLE 11

The lactalbumine according to Example 10 is replaced by a 8% solution of meat peptone, i.e. products of the proteolysis of the polypetides of meat. The yield is 93%.

EXAMPLE 12

Upon separation of the virus according to Example 2, the resulting product is examined as regards its microbial flora; the number of germs per ml is indicated hereinabove under A.

A similar separation is carried out, using however the buffer solution with an addition of 5 g of chloroform ($CHCl_3$) per liter with a view to selectively sterilizing the medium; the solution obtained (B) contains only very few germs. In another operation (C), the same antiseptic agent is added in a proportion of 5 g per liter to the buffer solution as well as to the liquid to be treated. The result is similar to that indicated under (B).

Furthermore, a certain amount of the same starting virus medium is submitted to zonal ultra-centrifugation after the usual addition of 0.01% merthiolate and 0.02% formaldehyde. The results obtained are indicated under D hereinbelow.

|     | Germs/ml |
| --- | --- |
| (A) Chromatography; without antiseptic agent | $10^5$ |
| (B) Chromatography; chloroform added to buffer | <10 |
| (C) Chromatography; chloroform added to buffer and to treated liquid | <10 |
| (D) Zonal ultracentrifugation; addition of merthiolate and formaldehyde | 3000 |

It should also be noted that the viruses obtained in operations A, B and C were alive, whereas the virus obtained in operation D was inactivated.

Furthermore, the products resulting from operations B and C (with addition of chloroform) retained the same degree of infection and the same hemoagglutinant power as those of the product of operation A the separation of which has been effected without any addition of antiseptic agent.

EXAMPLE 13

A virus solution similar to that used in operations A to D in Example 12, but corresponding to other virus strains, is submitted to separation in accordance with the operating mode described in Example 2.

In this manner, the liquids obtained when starting from 3 strains of influenza virus, to wit: A/URSS, A/TEXAS, B/HK, are examined.

In each case, chromatographic examination is carried out using 5 g of chloroform per liter of liquid and buffer, on the one hand, and without chloroform, on the other hand. Furthermore, comparative separation operations by means of zonal ultracentrifugation are also carried out.

The Table herein-below indicates the yields with respect to the starting liquid in each case, as well as the virus content expressed in international units per milligram of protein.

|  | VIRUS: | | |
| --- | --- | --- | --- |
|  | A/URSS | A/TEXAS | B/HK |
|  | Yield (%) | | |
| Chromatography with chloroform | 88 | 77.5 | 88 |
| Chromatography without chloroform | 81 | 71.5 | 81 |
| Zonal ultracentrifugation (merthiolate-formaldehyde | 72 | 50 | 63 |
|  | IU/mg protein | | |
| Chromatography with chloroform | 19,800 | 23,400 | 26,200 |
| Chromatography without chloroform | 15,900 | 12,100 | 19,200 |
| Zonal ultracentrifugation (merthiolate-formaldehyde) | 12,900 | 13,600 | 15,300 |

These results show that the addition of chloroform improves the yield as well as the concentration of the virus in the product obtained not only with respect to the conventional zonal ultra-centrifugation process, but even with respect to the improved exclusion chromatography process described in Examples 1 to 11.

In the present Example it has been found, as before, that the virus separated in the presence of chloroform is alive and has the same infection degree and the same hemoagglutinant power as the virus resulting from a chromatographic process using no chloroform. In contradistinction thereto, the virus separated by zonal ultra-centrifugation with conventional sterilization is inactivated.

EXAMPLE 14

In operations similar to those indicated under B and C in Example 12, bromoform in a concentration of about 1 g/l—which corresponds to the maximum solubility of $CHBr_3$ in water—has been used. In the final liquid, about 100 germs per ml have been found.

EXAMPLE 15

Replacing chloroform in Example 12 by tri-chloro-1,1,2-ethane in a proportion of 4 g per liter (solubility: 4.4 g per liter at 20° C.) also leads to obtaining a very reduced bacterial flora of less than 30 g/ml.

EXAMPLE 16

The operations of Example 2 are carried out in the column described in Example 1, however, without the second passivation, i.e. without treating a charge with allantoic liquid. The virus yield in this case is 70%.

EXAMPLE 17

When proceeding as indicated in Example 16, without the second passivation, the charge is constituted by the glass spheres described in Example 9, a yield of 64% is obtained, as compared to the 87% yield according to Example 9.

The values given in the present examples for the flow rate of eluant, the amount of liquid to be treated which is injected into the column, and the periodicity of such injection are not limitative but may be varied within comparatively wide limits.

EXAMPLE 18

Solutions of allantoic liquid infected with viruses are prepared in a manner known per se by means of various virus strains. 6 g/l of chloroform are introduced into these solutions.

The Table herein-below shows that the addition of chloroform does not modify the degree of infection and the hemoagglutinant power of these solutions.

|  | A/Victoria | A/X47 | HK 73 |
|---|---|---|---|
| HA degree prior to chloroform | 210 | 160 | 290 |
| after 24 hours | 210 | 160 | 280 |
| after 2 days | 180 | | |
| after 3 days | 230 | 160 | |
| after 5 days | | | 90 |
| Degree of infection | | | |
| without chloroform | $10^{7.0}$ | $10^{7.25}$ | $10^{5.5}$ |
| with chloroform | $10^{7.3}$ | $10^{7.25}$ | $10^{5.25}$ |

What is claimed is:

1. A process of separating a protein from an aqueous medium by liquid exclusion chromatography on a solid porous support which comprises contacting said support with the following successive agents:
   (a) an aqueous solution of a non-proteinic polymer;
   (b) an aqueous solution of a protein whose molecular weight is substantially less than the molecular weight of the protein to be separated;
   (c) said aqueous medium containing the protein to be separated; and
   (d) an eluent.

2. The process of claim 1, wherein said solid support is selected from the group consisting of silica gel and an alkali metal silicate in the form of particles having dimensions comprised between 40 and 200 microns, with an average pore diameter comprised between 5 and 200 nm.

3. The process of claim 1, wherein said non-proteinic polymer is selected from the group consisting of polyethylene-glycol, polypropylene-glycol, polybutylene-glycol, polyvinyl alcohol, polyvinyl pyrrolidone and (polyethylene-polypropylene)-glycol copolymers.

4. The process of claim 3, wherein said non-proteinic polymer has a molecular weight of 5,000 to 30,000, and wherein the concentration of said polymer in said aqueous solution is comprised between 0.5 and 5 g per liter.

5. The process of claim 1, wherein said lower molecular weight protein has a molecular weight lower than 100,000.

6. The process of claim 5 wherein said lower molecular weight protein is selected from the group consisting of albumins, gelatins, peptones and products of degradation of polypeptides, the molecular weight of said protein being not higher than 50,000.

7. The process of claim 1, wherein said lower molecular weight protein solution contains 0.2 to 20% by weight of said protein.

8. The process of claim 1, wherein said chromatographic support is eluted by means of an aqueous buffer solution having a pH value comprised between 5.5 and 7.5, and wherein an antiseptic agent is added to said buffer solution, said antiseptic agent being constituted by at least one halogenated lower aliphatic hydrocarbon and added in a proportion comprised within the range of the solubility of said agent in water, said proportion being 0.1 to 10 g/l.

9. The process of claim 1, wherein an antiseptic agent constituted by at least one halogenated lower aliphatic hydrocarbon is added to the liquid submitted to chromatography, said antiseptic agent being added in a proportion comprised within the range of the solubility of the said agent in water, said proportion being 0.1 to 10 g/l.

10. The process of claim 8, wherein said antiseptic agent is selected from the group consisting of monohalogenomethane, dihalogenomethane, trihalogenomethane, tetrahalogenomethane, monohalogenoethane, dihalogenoethane, trihalogenoethane, tetrahalogenoethane, monohalogenopropane, dihalogenopropane, trihalogenopropane and tetrahalogenopropane, wherein the halogen is selected from the group consisting of chlorine, bromine and iodine.

11. The process of claim 9, wherein said antiseptic agent is selected from the group consisting of monohalogenomethane, dihalogenomethane, trihalogenomethane, tetrahalogenomethane, monohalogenoethane, dihalogenoethane, trihalogenoethane, tetrahalogenoethane, monohalogenopropane, dihalogenopropane, trihalogenopropane and tetrahalogenopropane, wherein the halogen is selected from the group consisting of chlorine, bromine and iodine.

12. The process of claim 8, wherein said antiseptic agent is chloroform used in a proportion of 1 to 7 g/l.

13. The process of claim 9, wherein said antiseptic agent is chloroform, used in a proportion of 1 to 7 g/l.

14. The process of claim 1, wherein the protein to be separated is a virus.

15. The process of claim 14, wherein the liquid submitted to exclusion chromatography is a virus solution of comparatively high concentration.

16. The process of claim 15, wherein said liquid submitted to chromatography is a concentrated virus solution obtained by adsorption of the virus on an unsoluble polyalkylene-glycol complex having a polymerization degree of 80–1,200, with a calcium salt, said adsorption being followed by the separation of the adsorbate—and its redissolution in an aqueous solution of ethylene—diaminotetracetic acid or in an aqueous solution of sodium salt of said acid.

17. The process of claim 1 wherein said support is contacted with an aqueous sterilized buffer solution having a pH of about 5.5 to 7.5 between steps (b) and (c) and wherein eluent is an aqueous sterilized buffer solution having a pH of about 5.5 to 7.5.

18. A method of separating a virus from an aqueous medium containing said virus by liquid exclusion chromatography on a solid porous support wherein said support is silica gel or glass in the form of 40 to 200 microns particles having an average pore diameter of 5 to 200 nm, comprising subjecting said support to the following successive steps:
(a) contact with an aqueous solution of a non-proteinic polymer selected from the group consisting of polyethylene glycol, polypropylene glycol, polybutylene glycol, polyvinyl alcohol, polyvinyl pyrrolidone and (polyethylene-polypropylene) glycol polymer, said polymer having a molecular weight of 5,000 to 30,000 and present at a concentration of 0.5 to 5 grams per liter;
(b) contact with an aqueous solution containing 0.2 to 20% by weight of a protein whose molecular weight is lower than the molecular weight of the virus and does not exceed 100,000;
(c) rinsing with an aqueous buffer sterilized solution having a pH of about 5.5 to 7.5;
(d) contact with the aqueous medium containing the virus to be separated; and
(e) elution with an aqueous buffer sterilized solution having a pH of about 5.5 to 7.5.

* * * * *